United States Patent [19]

Fung et al.

[11] Patent Number: 5,258,538
[45] Date of Patent: Nov. 2, 1993

[54] 2,3-DISUBSTITUTED-1,3,2-OXAZAPHOS-PHACYCLOALKANES AS NUCLEIC ACID LINKING AGENTS

[75] Inventors: Steven Fung, Palo Alto; Sam L. Woo, Redwood City; Lloyd M. Smith, South Pasadena, all of Calif.

[73] Assignee: Applied Biosystems, Inc., Foster City, Calif.

[21] Appl. No.: 734,575

[22] Filed: Oct. 29, 1991

Related U.S. Application Data

[62] Division of Ser. No. 216,768, Jul. 8, 1988, Pat. No. 5,212,304.

[51] Int. Cl.$^5$ .............................. C07F 9/00
[52] U.S. Cl. ............................ 558/81; 536/25.32; 536/25.34
[58] Field of Search ............... 558/81; 536/25.34

[56] References Cited

U.S. PATENT DOCUMENTS

| | | | |
|---|---|---|---|
| 4,238,423 | 12/1980 | Sato et al. | 558/81 |
| 4,239,709 | 12/1980 | Sato | 558/81 |
| 4,263,231 | 4/1981 | Felcht | 558/81 |
| 4,751,319 | 6/1988 | Odorisio et al. | 558/76 |
| 4,831,178 | 5/1989 | Odorisio et al. | 558/76 |
| 5,043,465 | 8/1991 | Juge et al. | 558/72 |
| 5,075,481 | 12/1991 | Hofmann et al. | 558/76 |
| 5,075,483 | 12/1991 | Odorisio et al. | 558/81 |
| 5,075,484 | 12/1991 | Odorisio et al. | 558/81 |
| 5,142,083 | 8/1992 | Enlow et al. | 558/78 |

FOREIGN PATENT DOCUMENTS

| | | |
|---|---|---|
| 0245101 | 6/1969 | U.S.S.R. |
| 0410019 | 1/1974 | U.S.S.R. |
| 0469710 | 5/1975 | U.S.S.R. |

OTHER PUBLICATIONS

McGuigan et al., "Preparation of Phosphoglycerides by Phosphoramidite Chemistry," *J. Chem. Soc. Perk. Trans. I.* 2075, (1992).

Greenhalgh et al., "The Influence of Ring Strain on the Reactivity of Tervalent Phosphorus Compounds," *Chem. Comm.*, (1), 22 (1969).

Ueda et al., "Preparation of Acyclic Nucleoside Cyclic Phosphoramidates Having Antiviral and Anticancer Activities," *Chem. Abstr.*, 110(13), p. 740, Abstr. No. 115272x (1989); Abstr. of Japanese Kokai 63,165,373; only abstract provided.

Greene et al., *Protective Groups in Organic Synthesis*, 2nd Eds., John Wiley & Sons, Inc., New York, N.Y., 1981, see ch. 7, particularly pp. 309–316 and 349.

M. J. Gait, *Oligonucleotide Synthesis, A Practical Approach*, IRL Press, Washington, D.C., 1984, see chapter 2, particularly pp. 23–34.

M. H. Caruthers, "Gene Synthesis Machines: DNA Chemistry and Its Uses," *Science*, 230, 281–285 (1985).

Kurochkin et al., Chemical Abstract No. 91:57094s (1979).

*Primary Examiner*—John W. Rollins
*Assistant Examiner*—L. Eric Crane
*Attorney, Agent, or Firm*—Stephen C. Macevicz; Joseph H. Smith; Peter Dehlinger

[57] ABSTRACT

The compounds of the invention include novel linking agents comprising 2-substituted-3-protected-1,3,2-oxazaphosphacycloalkanes and their phosphoramidite precursors. The compounds of the invention further include conjugates of the above linking agents with oligonucleotides and polymer supports. The compounds of the present invention are useful for linking organic moieties, such as fluorescent or chromogenic dyes, to polymer supports and oligonucleotides, particularly single- and double-stranded DNA and RNA fragments.

27 Claims, No Drawings

2,3-DISUBSTITUTED-1,3,2-OXAZAPHOSPHACYCLOALKANES AS NUCLEIC ACID LINKING AGENTS

This is a divisional of copending application Ser. No. 07/216,768 filed Jul. 8, 1988, now U.S. Pat. No. 5,212,304.

BACKGROUND

The invention relates generally to organophosphorous compounds, and more particularly, to organophosphorous compounds for synthesizing amino-derivatized polymers, especially oligonucleotides.

Genes and gene control regions can now be routinely characterized and studied at the molecular level. This is possible because of several recent advances in the technology associated with manipulating and modifying deoxyribonucleic acid (DNA). Of particular importance have been advances in DNA sequencing, Maxam and Gilbert, "Sequencing End-Labeled DNA with Base-Specific Chemical Cleavages," and Smith, "DNA Sequence Analysis by Primed Synthesis," pgs. 499–560 and 560–580, respectively, in *Methods in Enzymology*, Grossman and Moldave, eds., Vol. 65 (Academic Press, New York, 1980); the isolation of a large number of host restriction modification enzymes, Roberts, "Dictionary of Restriction Endonucleases," in *Methods in Enzymology*, Wu, ed., Vol. 68 (Academic Press, New York, 1979); and the construction of vectors for cloning and amplifying defined DNA sequences, e.g. Bolivar and Backman, "Plasmids of *Escherichia coli* as Cloning Vectors," in *Methods in Enzymology*, Wu, ed., Vol. 68 (Academic Press, New York, 1979).

Many of these new techniques require that DNA fragments or oligonucleotides be labeled or attached to polymer supports. DNA sequencing techniques and gene probes, which can be used to help locate natural genes of commercial or scientific importance, require the use of labeled oligonucleotides. Until recently, all DNA sequencing techniques relied on radioactive labels for distinguishing oligonucleotide fragments separated by electrophoresis. Radioactive labels are highly sensitive, and can be incorporated without steric hinderance, or other chemical side effects. However, their use poses a laboratory health hazard, which requires that they receive special handling and disposal. Moreover, their use is not amenable for rapid automatic sequencing of oligonucleotides, as nucleoside-specific radioactive labels are not available for practical identification of different nucleotide bases, and radiation detection techniques such autoradiography and scintillation counting are too time consuming. As a consequence, other non-radioactive labelingtechniques have been sought, such as fluorescent and colorimetric labeling, which depend on the ability to covalently link a fluorescent or chromogenic molecule to an oligonucleotide.

Chu et al, in "Derivatization of Unprotected Polynucleotides," *Nucleic Acids Research*, Vol.11, pgs. 6513–6529(1983), disclose a method for attaching amines to the terminal 5'-phosphates of oligonucleotides. One object of the method is to provide a means for attaching organic labeling molecules to oligonucleotides by way of an amine linkage. The method involves treating the oligonucleotides with a carbodiimide.

Chollet and Kawashima, in "Biotin-Labeled Synthetic Oligodeoxyribonucleotides: Chemical Synthesis and Uses as Hybridization Probes," *Nucleic Acids Research*, Vol.13, pgs. 1529–1541 (1985), disclose the use of the method of Chu et al to attach biotin to the 5'-phosphate of an oligonucleotide. The reported yields of 50-70% are below that needed for use in automatic synthesizers, and the carbodiimide can cause unwanted modifications to oligonucleotide bases in the course of the reaction.

Smith et al, in "Synthesis of Oligonucleotides Containing an Aliphatic Amino Group at the 5' Terminus: Synthesis of Fluorescent DNA Primers for Use in DNA Sequence Analysis," *Nucleic Acids Research*, Vol.13, pgs. 2399–2412 (1985), disclose a protected amino-derivatized nucleoside phosphoramidite for linking fluorescent or colorimetric tags to oligonucleotide fragments. While the linker is highly useful for attaching base-specific labels to the 5' terminus of oligonucleotides, the protected-amine phosphoramidite is not readily purified.

Connolly and Rider, in "Chemical Synthesis of Oligonucleotides Containing a Free Sulphydryl Group and Subsequent Attachment of Thiol Specific Probes," *Nucleic Acids Research*, Vol. 13, pgs. 4485–4502 (1985), disclose the synthesis of oligonucleotides having a trityl-protected sulphur attached via a two, three, or six carbon chain to the 5' phosphate of the oligonucleotide.

Apart from linking labeling agents to oligonucleotides, there is great interest in immobilizing various molecules on polymer supports, such as catalysts, enzymes, microorganisms, affinity reagents, immunoadsorbents, and the like, for both preparative and analytical uses, e.g. Schott, *Affinity Chromatography* (Marcel Dekker, Inc., New York,1984), and Mosbach, ed., *Methods in Enzymology*, Vol.44, "Immobilized Enzymes," (Academic Press, New York, 1976). Of particular interest in this field are means for immobilizing molecules and cells by covalent bonds.

SUMMARY OF THE INVENTION

The compounds of the invention include novel linking agents comprising 2-substituted-3-protected-1,3,2-oxazaphosphacycloalkanes and their phosphoramidite precursors. The compounds of the invention further include conjugates of the above mentioned linking agents with oligonucleotides, conjugates of the above mentioned linking agents with polymer supports, and conjugates comprising dyes linked to oligonucleotides by the above mentioned linking agents. The present invention relates to compounds that are useful for linking organic moieties, such as fluorescent and chromogenic dyes, to DNA fragments and oligonucleotides, particularly single-stranded DNA and RNA, and for linking DNA fragments, oligonucleotides, proteins, and the like to polymer supports. The compounds and their conjugates are useful in automated and manual DNA and RNA synthesis and sequence analysis, construction of gene probes, affinity techniques, and the like. In particular, the cyclic embodiments of the linking agents of the invention advantageously overcome deficiencies associated with currently available linking methods by providing more readily purified linking agents.

DESCRIPTION OF THE INVENTION

The linking compounds of the present invention include 2-substituted-3-protected-1,3,2-oxazaphosphacycloalkanes defined by the formula:

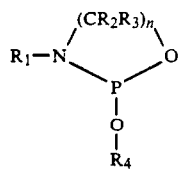

wherein:
  n is in the range of 2 to 4, preferably in the range of 2 to 3, and most preferably is equal to 2.
  $R_1$ represents an amino protection group, preferably either acid-labile or base-labile, e.g. as described by Greene, in *Protective Groups in Organic Synthesis* (John Wiley & Sons, New York, 1981), chapter 7, which chapter is incorporated by reference. Preferably base-labile protection groups when taken together with the nitrogen of the heterocycle or that of its precursor, are base-labile amide and carbamate protection groups, preferably trihaloacetyls, acetoacetyl, and fluorenylmethyl carbamates, particularly 9-fluorenylmethyl carbamate and 9-(2-sulfo)fluorenylmethyl carbamate, and most preferably trifluoroacetyl. Preferable acid-labile protection groups include trityls, and their lower (containing from 1-3 carbon atoms) alkoxy derivatives, particularly 4-monomethoxytrityl and 4,4'-dimethoxytrityl.
  $R_2$ and $R_3$ are chosen so that (1) the likelihood that they sterically hinder the cyclization of the compound of Formula I is minimized, (2) the ring electron density of the heterocycle of Formula I is reduced, because it is thought that this will enhance the reactivity of the N-P bond in the compound of Formula I to hydroxyl groups, and (3) the molecular weight of the compound of Formula I is minimized to increase the likelihood that it can be purified by distillation. $R_2$ and $R_3$ taken separately each represent hydrogen, lower alkyl, lower substituted alkyl, particularly halo-, cyano-, or nitro- substituted lower alkyl, lower acyl, cyano, halo, and nitro; more preferably $R_2$ and $R_3$ taken separately each represent hydrogen, lower alkyl, and lower haloalkyl; and most preferably $R_2$ and $R_3$ represent hydrogens.
  $R_4$ represents alkyl, alkenyl, aryl, aralkyl, or cycloalkyl containing up to 10 carbon atoms. More preferably, $R_4$ represents lower alkyl; electron-withdrawing beta-substituted ethyl, particularly beta-trihalomethyl-, beta-cyano-, beta-sulfo-, beta-nitro-substituted ethyl, or the like; electron-withdrawing substituted phenyl, particularly halo-, sulfo-, cyano-, or nitro-, substituted phenyl; or electron-withdrawing substituted phenylethyl. Most preferably, $R_4$ represents methyl, beta-cyanoethyl, or 4-nitrophenylethyl.

The term "lower alkyl" as used herein denotes straight-chain and branched-chain alkyl groups containing from 1-6 carbon atoms, e.g. methyl, ethyl, propyl, isopropyl, tert-butyl, isobutyl, sec-butyl, neopentyl, tert-pentyl, and the like. "Lower substituted alkyl" denotes lower alkyl having electron-withdrawing substituents, such as halo, cyano, nitro, sulfo, or mono-, di-, or trihalomethyl, or the like. "Lower haloalkyl" denotes a lower alkyl with one or more halogen atom substituents, usually fluoro, chloro, bromo, or iodo. "Lower acyl" denotes an acyl containing from 1-7 carbon atoms wherein the non-double bonded carbons comprise a lower alkyl, possibly having halo-, cyano-, or nitro- substituents. "Electron-withdrawing" denotes the tendency of a substituent to attract valence electrons of the molecule of which it is apart, i.e. it is electronegative.

A special case of the above-described linking agent includes bicyclic compounds defined by the formula:

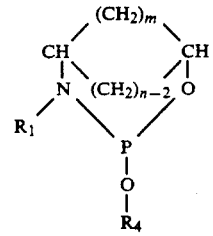

Formula II wherein m is in the range of 1 to 3, and n, $R_1$, and $R_4$ are as defined above. More preferably m is in the range of 1 to 2; and most preferably m is 1. The lower cycloalkyl attached to the oxazaphospha-heterocycle is thought to introduce ring strain into the heterocycle making the nitrogen-phosphorous bond more reactive.

The linking compounds of the invention also include the phosphoramidite precursors to the above 2-substituted-3-protected-1,3,2-oxazaphosphacycloalkanes, the precursors being defined by the formula:

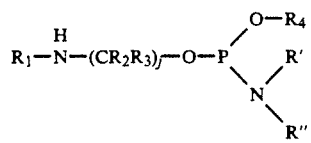

Formula III wherein:
  $R_1$, $R_2$, $R_3$, and $R_4$ are as indicated above;
  j is in the range of 2 to 10, more preferably in the range of 2 to 4, and most preferably j is in the range or 2 to 3 (it is believed that this latter range results in a precursor possessing the most favorable steric configuration for cyclization); and
  R' and R" taken separately each represent alkyl, aralkyl, cycloalkyl, and cycloalkylalkyl containing up to 10 carbon atoms. Preferably R' and R" taken separately represent lower alkyl, and most preferably when the above phosphoramidites are used directly as linking agents, R' and R" taken separately are sterically hindering lower alkyls which enhance the chemical stability of the phosphoramidites, and hence their shelf lives. Such sterically hindering lower alkyls include isopropyl, t-butyl, isobutyl, sec-butyl, neopentyl, tert-pentyl, isopentyl, sec-pentyl, and the like. Most preferably, when the above phosphoramidites are used as precursors to the above-described oxazaphospha-heterocycle, R' and R" taken separately are isopropyl.
  R' and R" taken together form an alkylene chain containing up to 5 carbon atoms in the principal chain and a total of up to 10 carbon atoms with both terminal valence bonds of said chain being attached to the nitrogen atom to which R' and R" are attached; or R' and R" when taken together with the nitrogen atom to which they are attached form a saturated nitrogen heterocycle which may contain one or more additional heteroatoms from the group consisting of nitrogen, oxygen, and sulfur. More preferably, R' and R" taken together and with the nitrogen to which they are attached represent pyrrolidino, morpholino, or piperidino. Most preferably, R' and R" taken together and with the nitrogen to which they are attached represent morpholino.

The phosphoramidite precursors to the above-described 2-substituted-3-protected-1,3,2-oxazaphosphacycloalkanes include substituted lower cycloalkanes defined by the formula:

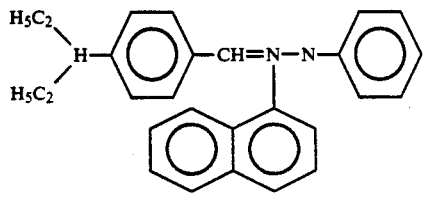

wherein $R_1$, $R_4$, R', and R" are as indicated above, and t is in the range of 0 to 8, and s is in the range of 0 to 8, subject to the condition that s+t is in the range of 1 to 8, more preferably t is in the range of 0 to 2, and s is in the range of 1 to 3, still more preferably t is 0 and s is in the range of 1 to 2, and most preferably t is 0 and s is 1.

Conjugates of the present invention include triester phosphite and triester and diester phosphate compounds of the formula:

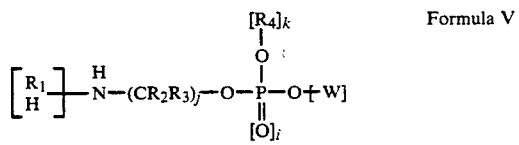

Formula V wherein:
i is 0 or 1 (where i=0 indicates phosphite, and i=1 indicates phosphate);
k equals 1 (where k=0 indicates diester, and k=1 indicates triester) whenever i equals 0, or k equals 0 or 1 whenever i equals 1;
j, $R_1$, $R_2$, $R_3$, and $R_4$ are as indicated above; and W represents an oligonucleotide, a polymer support, or an oligonucleotide linked to a polymer support. Oligonucleotides include fragments of single-stranded and double-stranded RNA, and fragments of single- and double-stranded DNA. Preferably the linking agent is conjugated to the terminal 5' carbon of an oligonucleotide, the terminal 3' carbon of an oligonucleotide, or the terminal 2' carbon of RNA. More preferably, the linking agent is conjugated to the terminal 5' carbon of an oligonucleotide, and most preferably the linking agent is conjugated to the terminal 5' carbon of a fragment of single-stranded DNA.

Polymer supports may have a variety of forms and compositions. The polymer support can be derived from naturally occurring materials, naturally occurring materials which are synthetically modified, and synthetic materials. Of particular interest are polysaccharides, particularly crosslinked polysaccharides, such as agarose, which is available as Sepharose, dextran, available as Sephadex and Sephacyl, cellulose, starch and the like (Sepharose, Sephadex, and Sephacyl being trademarked products of Pharmacia Fine Chemicals). Other materials include polyacrylamides, polystyrenes, polyvinyl alcohols, copolymers of hydroxyethyl methacrylate and methyl methacrylate, silicones, teflons glasses, cells, or the like. In addition to solid supports in the form of particles and the like, the polymer support may also be in the form of liquid particles comprising a lipophilic or amphiphilic membrane, which serves to contain an internal fluid and define a space. Such particles include vesicles, cells, and liposomes. Preferably W represents an insoluble polymer support having hydroxyl functionalities. The linking agents of the invention are attached to polymer supports having hydroxyl functionalities by following the procedures generally described below for attaching the linking agents to oligonucleotides.

The bracket on the lefthand side of Formula V (enclosing H and $R_1$) indicates that this embodiment includes both the protected and deprotected forms of the compound.

Oligonucleotides are linked to polymer supports by standard techniques of affinity chromatography or, for example, by linking means disclosed by Caruthers et al. in U.S. Pat. Nos. 4,458,066 and 4,415,732, or the like.

The triester phosphite and triester and diester phosphate conjugates of the present invention further include compounds of the formula:

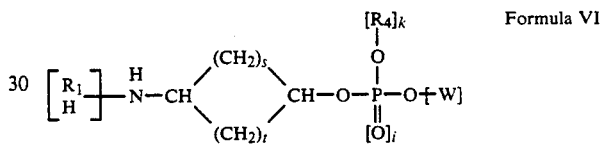

Formula VI wherein i, k, s, t, $R_1$, $R_4$, and W are as indicated above.

Generally the triester phosphate compounds of the invention are readily obtained from the above-defined phosphite conjugates by oxidation, e.g. with the use of $I_2$ in water, 2,6-lutidine and tetrahydrofuran. Oxidation is extremely rapid (1-2 minutes).

The diester phosphate conjugates of the invention are readily obtained from the above-defined triester phosphates by standard techniques, for example when $R_4$ is methyl, the diester phosphates are obtained from the triester phosphates by treatment with thiophenol/triethylamine for about 30 minutes.

The general procedure for synthesizing the phosphoramidite precursors of Formulas III and IV comprises the following steps. Halo-substituted-N,N-di-substituted-O-substituted phosphine, defined by the formula:

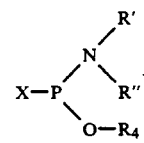

wherein X is a halogen, usually chloro, and R', R", and $R_4$ are as indicated above, is reacted with an amino-protected alcohol amine defined by the formula:

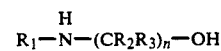

wherein $R_1$, $R_2$, and $R_3$ are as indicated above, in an aprotic solvent, such as dichloromethane, or the like, containing a non-nucleophilic base, for example a trialkylamine, such as N,N-diisopropylethyl amine, or the like, which absorbs the halogen acid released during the reaction. Preferably the reaction takes place under an inert atmosphere, such as argon. Acid conditions in the reaction mixture should be avoided as acid causes the amine of the phosphoramidite product to protonate, and thereby become reactive. The non-nucleophilic base reduces the likelihood of side reactions between the base and activated phosphoramidites.

Whenever the alkyl moiety, i.e. —$(CR_2R_3)_n$—, of the amino-protected alcohol amine is cycloalkyl, e.g. as in Formula IV, the amide or carbamate moiety of the alcohol amine is preferably in the cis configuration with the hydroxy; otherwise, formation of the oxazaphosphaheterocycle becomes unlikely, or even impossible, because of the spacial separation of the two groups.

After reacting the above materials, the reaction mixture, hereinafter referred to as the first reaction mixture, is washed with a mildly basic solution to remove salts of the non-nucleophilic base. Finally, the first reaction mixture is dried, e.g. with $MgSO_4$, $Na_2SO_4$, or the like, to give the phosphoramidite precursor.

The heterocycles of Formulas I and II are obtained by heating the appropriate precursor represented by Formulas III or IV, respectively, to form a second reaction mixture, and then separating the heterocycle from the mixture. The necessary amount of heating, i.e. temperature and duration, varies with different embodiments of the invention, preferably heating includes raising the precursor to a temperature within the range of about 25° to 250° C., more preferably from about 25° to 150° C., and most preferably from about 25° to 100° C. The choice of method of separation depends on the nature of the substituent groups, $R_1$, $R_2$, $R_3$, and $R_4$. For example, as a rough approximation when the aggregate molecular weight of the substituents is sufficiently low, the steps of heating and separating can be accomplished by distilling. Other methods of separation include crystallization and chromatography. Preferably conjugates of oligonucleotides and linking agents of the invention are formed by attaching the linking agent to oligonucleotides synthesized by the solid phase synthetic methods developed by Caruthers and his coworkers, e.g. Caruthers et al., pgs. 1–17, in *Genetic Engineering*, Vol. 4, Setlow and Hollaender, Eds. (Plenum Press, New York, 1982), and Caruthers et al., U.S. Pat. No. 4,458,066. Attachment of the linking agent occurs as the final step in the synthetic process; that is, the linking agent is attached to the oligonucleotide as if it were a nucleotide subunit in the Caruthers et al. method.

The following examples serve to illustrate the present invention. The concentrations of reagents, temperatures, and values of other variable parameters are only to exemplify the application of the present invention and are not to be considered as limitations thereof.

EXAMPLE I

Synthesis of the phosphoramidite precursor of 2-methoxy-3-trifluoroacetyl-1,3,2-oxazaphosphacyclopentane Chloro-N,N-diisopropylaminomethoxy phosphine (5.0 ml, available form Aldrich Chemical Co., Milwaukee, Wis.) was added dropwise at 0° C. to a stirred solution of N-(2-hydroxyethyl)-2,2,2-trifluoroacetamide (3.9 g) and diisopropylethylamine (5.0 ml) in dichloromethane (about 40 ml) under argon. (N-(2-hydroxyethyl)-2,2,2-trifluoroacetamide is synthesized following the procedures disclosed by Lazarus and Benkovic in *J.*
*Am. Chem. Soc.*, Vol. 101, pgs. 4300–4312 (1979): Ethyl trifluoroacetate (56.8 g, 0.4 mol) in 50 mL of chloroform is added dropwise to a stirred solution of 24.4 g (0.4 mol) of ethanolamine in 50 mL of chloroform. The solution is stirred at room temperature for 5 h, rotary evaporated to remove the solvent, and distilled at 115° C. (4.3 Torr) to give 58.5 g of oil that crystallized upon scratching.) After stirring at room temperature for 0.5 hours the reaction mixture was washed twice with 0.2M potassium carbonate solution and once with brine, dried ($MgSO_4$), and concentrated under reduced pressure to give N-(2-(N',N'-diisopropylaminomethoxyphosphinyloxy)ethyl)-2,2,2-trifluoroacetamide as a colorless liquid (7.77 g).

$^1$H-NMR ($CD_2Cl_2$): δ3.6 (6H, m), 3.4 (3H, d, J=12), 1.2 (12H, d, J=6.5)

$^{31}$P-NMR ($CD_2Cl_2$, $^1$H-decoupled): δ149(s)

EXAMPLE II

Synthesis of the phosphoramidite precursor of 2-methoxy-3-trifluoroacetyl-1,3,2-oxazaphosphacyclohexane Chloro-N,N-diisopropylaminomethoxy phosphine (3.7 ml) was added dropwise at 0° C. to a stirred solution of N-(3-hydroxypropyl)-2,2,2-trifluoroacetamide (2.9 g, synthesized from 3-amino-1-propanol and ethyltrifluoroacetate in a manner similar to that disclosed by Lazarus and Benkovic, *J. Amer. Chem. Soc.*, Vol.101, pgs. 4300–4312 (1979)) and diisopropylethylamine (3.7 ml) in dichloromethane (about 20 ml) under argon. After stirring at room temperature for 3 hours, the reaction mixture was poured into hexane (100 ml) and stirred. The mixture was allowed to settle and the supernatant was separated and concentrated under reduced pressure to give N-(3-(N',N'-diisopropylaminomethoxyphosphinyloxy)propyl)-2,2,2-trifluoroacetamide as a colorless liquid (5.2 g).

$^{31}$P-NMR ($CH_2Cl_2$, $^1$H decoupled): δ149 (s)

EXAMPLE III

Synthesis of 2-methoxy-3-trifluoroacetyl-1,3,2-oxazaphosphacyclopentane

N-(2-(N',N'-diisopropylaminomethoxyphosphinyloxy)ethyl)-2,2,2-trifluoroacetamide (7.7 g) was distilled (58°–59° C. at 0.8 Torr) to quantitatively yield 2-methoxy-3-trifluoroacetyl-1,3,2-oxazaphosphacyclopentane as a colorless liquid.

IR (film): 1705, 1420, 1230, 1200, 1160, 1020, 965 cm$^{-1}$ $^1$H-NMR ($CD_2Cl_2$) δ4.45 (2H, m), 3.65 (2H, m), 3.60 (3H, d, J=12)

$^{31}$P-NMR ($CD_2Cl_2$, $^1$H decoupled): δ132(s), 125 (q, J=61)

MS: m/e 217 (M$^+$), 197, 148, 136, 123, 120, 109, 92, 79, 70(100), 69, 62

EXAMPLE IV

Attaching 2-methoxy-3-trifluoroacetyl-1,3,2-oxazaphosphacyclopentane to the 5' terminus of an oliqonucleotide Attachment of 2-methoxy-3-trifluoroacetyl-1,3,2-oxazaphosphacyclopentane to a 5' hydroxyl of an oligonucleotide was performed on an Applied Biosystems 380A DNA synthesizer (Applied Biosystems, Foster City, Calif.), or comparable instrument. Caruthers et al, U.S. Pat. Nos. 4,458,066; Caruthers et al, 4,415,732; and Caruthers et al, "New Methods for Synthesizing Deoxyoligonucleotides," in *Genetic Engineering,* Vol. 4, pgs. 1–17 (Plenum Press, New York, 1982) provide detailed descriptions of the chemistry used by the Applied Biosystems 380A DNA synthesizer. Accordingly, these references are incorporated by reference for those descriptions. 2-Methoxy-3-trifluoroacetyl-1,3,2-oxazaphosphacyclopentane was used as a 0.2M acetonitrile solution in combination with 0.5M tetrazole/acetonitrile solution to form an activated reagent in the synthesis cycle. The normal synthesizer cycle was modified only during the addition of the activated reagent in the following manner. The activated reagent was added twice with 1 hour wait times after each addition. The coupling yields were about 95%. Normal deprotection with thiophenol/triethylamine and then ammonium hydroxide gave a 5'-aminoethylphosphate oligonucleotide. Similar yields were obtained when the activated reagent comprised an acetonitrile solution containing 0.2M 2-methoxy-3-trifluoroacetyl-1,3,2-oxazaphosphacyclopentane and 0.1M 4-dimethylaminopyridine. In this case the modified activator reagent was added once, and allowed to react for about 15 minutes.

EXAMPLE V

Attaching 2-methoxy-3-trifluoroacetyl-1,3,2-oxazaphosphacyclopentane to the 3' terminus of an oligonucleotide Attachment is accomplished in substantially the same manner as described in Example IV, except the oligonucleotide is synthesized in the 3' direction in accordance with the procedure generally described in Caruthers et al, U.S. Pat. No. 4,458,066. (Roughly the difference is that the oligonucleotide is synthesized from 5' N,N-diisopropylaminophosphoramidites of 3'-protected nucleosides instead of 3' N,N-diisopropylaminophosphoramidites of 5'-protected nucleosides. Alternatively, the oligonucleotide is synthesized in the 3' direction using the phosphotriester method of Khorana and Itakura (i.e., Khorana, *Science,* Vol. 203, pgs. 614–625 (1979); Itakura et al. *J. Biol. Chem.,* Vol. 250, pgs. 4592–4600, both of these references being incorporated by reference), or its modification by others, for example Letsinger and Mahaderan, *J. Am. Chem. Soc.,* Vol. 187, pgs. 3526—(1965). In any case the linking agent is attached as a final addition in place of a nucleotide.

EXAMPLE VI

Attaching Fluorescein isothiocyanate (FITC) to a 5' aminoethylphosphate oligonucleotide A dimethylformamide solution of fluorescein-6-isothiocyanate (25 microliters at a concentration of 10 mg/ml, e.g. available form Molecular Probes, Inc., Junction City, Ore.) was added to a solution of 5'-aminoethylphosphate TCCCAGTCACGACGTT (0.020 micromole, unpurified material being made on an Applied Biosystems 380A DNA synthesizer; here T=thymidine, C=cytidine, G=guanosine, and A=adenosine) in water (200 microliters) and 1M NaHCO$_3$/Na$_2$CO$_3$ buffer, pH 9.0 (25 microliters). The resulting solution was stored in the dark at room temperature for at least 6 hours. To remove the unconjugated dye, the reaction mixture was passed through an equilibrated 10 ml Sephadex (trademark of Pharmacia Fine Chemicals) G-25 (medium) column with water. The band of colored material in the excluded volume was collected. The crude 5'-fluorescein aminoethylphosphate oligonucleotide was purified by HPLC (e.g. Perkin-Elmer Series 4, or comparable instrument) on a Vydac C18 column (No. 218TP54), or the like, in a linear gradient of 10–20% acetonitrile/0.1M triethylammonium acetate, pH 7.0.

We claim:

1. A compound of the formula

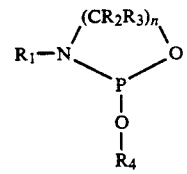

wherein:

n is in the range of 2 to 4;

$R_1$ is an amino protection group;

$R_2$ and $R_3$ taken separately each represent hydrogen; alkyl having from 1 to 6 carbon atoms; halo-, cyano-, sulfo-, halomethyl-, dihalomethyl-, or trihalomethyl- substituted alkyl having from 1 to 6 carbon atoms; cycloalkyl having from 3 to 6 carbon atoms; acyl having from 1 to 7 carbon atoms; cyano; halo; or nitro; and $R_4$ is alkyl, alkenyl aryl, aralkyl, or cycloalkyl containing up to 10 carbon atoms.

2. A compound according to claim 1 wherein n is in the range of 2 to 3.

3. A compound according to claim 2 wherein $R_1$ taken together with the nitrogen to which it is attached represents a base-labile amide or carbamate protection group, and $R_4$ is alkyl having from 1 to 6 carbon atoms; halo-, cyano-, nitro-, sulfo-, halomethyl-, dihalomethyl-, or trihalomethyl-beta-substituted ethyl; halo-, cyano-, nitro-, sulfo-, halomethyl-, dihalomethyl-, or trihalomethyl-substituted phenylethyl; or halo-, cyano-, nitro-, sulfo-, halomethyl-, dihalomethyl-, or trihalomethyl-substituted phenyl.

4. A compound according to claim 3 wherein $R_4$ is alkyl having from 1 to 6 carbon atoms; beta-trihalomethyl-, beta-nitro-, beta-sulfo-, or beta-cyano-substituted ethyl; halo-, nitro-, sulfo-, or cyano- substituted phenyl; or halo-, nitro-, sulfo-, or cyano- substituted phenylethyl.

5. A compound according to claim 4 wherein $R_4$ is methyl, beta-cyanoethyl, or 4-nitrophenylethyl.

6. A compound according to claim 5 wherein $R_4$ is methyl, or beta-cyanoethyl.

7. A compound according to claim 3 wherein $R_1$ is trihaloacetyl, acetoacetyl, or fluorenylmethyl carbamate.

8. A compound according to claim 7 wherein $R_4$ is alkyl having from 1 to 6 carbon atoms; beta-trihalomethyl-, beta-nitro-, beta-cyano-, or beta-sulfo-substituted ethyl; halo-, nitro-, cyano-, or sulfo- substituted phenyl; or halo-, nitro-, cyano-, or sulfo- substituted phenylethyl.

9. A compound according to claim 8 wherein $R_4$ is methyl, beta-cyanoethyl, or 4-nitrophenylethyl.

10. A compound according to claim 9 wherein $R_4$ is methyl, or beta-cyanoethyl.

11. A compound according to claim 7 wherein $R_1$ is trifluoroacetyl, acetoacetyl, 9-(2-sulfo)fluorenylmethyl carbamate, or 9-fluorenylmethyl carbamate.

12. A compound according to claim 11 wherein $R_4$ is methyl, beta-cyanoethyl, or 4-nitrophenylethyl, and wherein $R_2$ and $R_3$ are hydrogens.

13. A compound according to claim 12 wherein $R_1$ is trifluoroacetyl or acetoacetyl, and wherein $R_4$ is methyl or beta-cyanoethyl.

14. A compound according to claim 2 wherein $R_1$ is an acid-labile amino protection group.

15. A compound according to claim 14 wherein $R_4$ is alkyl having from 1 to 6 carbon atoms; beta-trihalomethyl-, beta-nitro-, beta-sulfo-, or beta-cyano-substituted ethyl; halo-, nitro-, cyano-, or sulfo-substituted phenyl; or halo-, nitro-, cyano-, or sulfo-substituted phenylethyl.

16. A compound according to claim 15 wherein $R_1$ is trityl or alkoxy-substituted trityl, wherein said alkoxy has from 1 to 6 carbon atoms.

17. A compound according to claim 16 wherein $R_1$ is 4-monomethoxytrityl or 4,4'-dimethoxytrityl.

18. A compound according to claim 17 wherein $R_4$ is methyl or beta-cyanoethyl.

19. 2-methoxy-3-trifluoroacetyl-1,3,2-oxazaphosphacyclopentane.

20. 2-methoxy-3-trifluoroacetyl-1,3,2-oxazaphosphacyclohexane.

21. A compound of the formula:

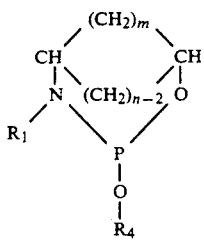

wherein:

m is in the range of 1 to 3;
n is in the range of 2 to 3;
$R_1$ is an amino protection group; and
$R_4$ is alkyl, alkenyl, aryl, aralkyl, or cycloalkyl containing up to 10 carbon atoms.

22. A compound according to claim 21 wherein:
m is in the range of 1 to 2;
n is 2;
$R_1$ taken together with the nitrogen atom to which it is attached is a base-labile amide or carbamate protection group; and
$R_4$ is alkyl having from 1 to 6 carbon atoms; beta-trihalomethyl-, beta-cyano-, beta-nitro-, or beta-sulfo-substituted ethyl; halo-, nitro-, cyano-, or sulfo-substituted phenyl; or halo-, nitro-, cyano-, or sulfo-substituted phenylethyl.

23. A compound according to claim 22 wherein $R_1$ is trihaloacetyl, acetoacetyl, or fluorenylmethyl carbamate, and $R_4$ is methyl, beta-cyanoethyl, or 4-nitrophenylethyl.

24. A compound according to claim 23 wherein $R_1$ is trifluoroacetyl, or acetoacetyl, and $R_4$ is methyl or beta-cyanoethyl.

25. A compound according to claim 21 wherein:
m is in the range of 1 to 2;
n is 2;
$R_1$ is an acid-labile amino protection group; and
$R_4$ is lower alkyl; beta-trihalomethyl-, beta-cyano-, beta-nitro-, or beta-sulfo-substituted ethyl; halo-, nitro-, cyano-, or sulfo-substituted phenyl; or halo-, nitro-, cyano-, or sulfo-substituted phenylethyl.

26. A compound according to claim 25 wherein $R_1$ is trityl or alkoxy-substituted trityl wherein said alkoxy has from 1 to 6 carbon atoms, and $R_4$ is methyl, beta-cyanoethyl, or 4-nitrophenylethyl.

27. A compound according to claim 26 wherein $R_1$ is 4,4'-dimethoxytrityl or 4-monomethoxytrityl, and $R_4$ is methyl or beta-cyanoethyl.

* * * * *

UNITED STATES PATENT AND TRADEMARK OFFICE
CERTIFICATE OF CORRECTION

PATENT NO. : 5,258,538

DATED : November 2, 1993

INVENTOR(S) : Steven Fung, Sam L. Woo, LLoyd M. Smith

It is certified that error appears in the above-indentified patent and that said Letters Patent is hereby corrected as shown below:

On the title page: item [21]Appl. No.: delete "734,575" and insert --784,575 --.

Col. 1, line 51, insert --as -- between "such" and "auto-radiography."

Column 6, line 1, delete "A'" and insert --W' --; line 19 delete "ploymer" and insert --polymer --.

Signed and Sealed this

Tenth Day of January, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,258,538

DATED : November 2, 1993

INVENTOR(S) : Steven Fung, et. al.

It is certified that error appears in the above-identified patent and that said Letters Patent is hereby corrected as shown below:

On the cover page at item [21], "734,575" should be --784,575--.
Column 1, line 52, insert --as-- between "such" and "auto-radiography."
Column 6, line 8, delete "A' " and insert --W'--; line 19 delete "ploymer" and insert --polymer --.
Column 3, line 1, insert --Formula I-- at the upper right hand side of the structure.
Column 4, at about line 42, "or 2 to 3" should be --of 2 to 3--.
Column 5, lines 12-20, the captioned structure should be replaced with the following:

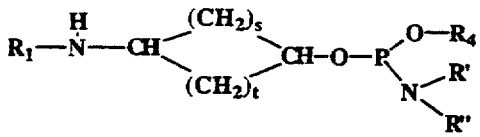

--.

This certificate supersedes Certificate of Correction issued January 10, 1995.

Signed and Sealed this

Twenty-ninth Day of August, 1995

BRUCE LEHMAN

*Attest:*

*Attesting Officer*     *Commissioner of Patents and Trademarks*